United States Patent [19]

Müller

[11] Patent Number: 4,782,185

[45] Date of Patent: Nov. 1, 1988

[54] PROCESS FOR THE PREPARATION OF 4-NITRODIPHENYLAMINES

[75] Inventor: Ernst W. Müller, Leverkusen, Fed. Rep. of Germany

[73] Assignee: Bayer Aktiengesellschaft, Leverkusen, Fed. Rep. of Germany

[21] Appl. No.: 12,483

[22] Filed: Feb. 9, 1987

[30] Foreign Application Priority Data

Feb. 19, 1986 [DE] Fed. Rep. of Germany ....... 3605197

[51] Int. Cl.$^4$ .............................................. C07C 85/04
[52] U.S. Cl. .................................... 564/406; 564/414; 564/435
[58] Field of Search ......................... 564/406, 414, 435

[56] References Cited

U.S. PATENT DOCUMENTS 4,435,599  3/1984  Sturm ................................. 564/433
4,683,332  7/1987  Sturm ................................. 564/414

FOREIGN PATENT DOCUMENTS 3308659  10/1984  Fed. Rep. of Germany ...... 564/406

OTHER PUBLICATIONS

Szmadja, J. et al., *Chemical Abstracts*, vol. 91, No. 192970q, (1979).

*Primary Examiner*—Glennon H. Hollrah
*Assistant Examiner*—John A. Sopp
*Attorney, Agent, or Firm*—Connolly and Hutz

[57] ABSTRACT

With a far shorter reaction time, azeotropic distillation of the water in the condensation of 4-nitrohalogenobenzenes and primary aromatic amines or formyl derivatives thereof in the presence of potassium carbonate and, if appropriate, copper compounds can be dispensed with if the reaction is carried out in the presence of Al metal, Mg metal or Zn metal or mixtures or alloys of these metals.

4 Claims, No Drawings

PROCESS FOR THE PREPARATION OF 4-NITRODIPHENYLAMINES

The invention relates to a process for the preparation of 4-nitrodiphenylamines by reaction of 4-nitrohalogenobenzenes with primary aromatic amines in the presence of potassium carbonate and copper compounds, or with the formyl derivatives of primary aromatic amines in the presence of potassium carbonate.

The reaction of halogenonitrobenzenes with aromatic amines or with formyl derivatives thereof has already been known for a long time. Thus, it is known from German Patent Specification 185,663 that the reaction can be carried out in the presence of alkali metal carbonates and copper compounds as catalysts.

It is also known that the reaction, which takes an exceptionally long time, can be accelerated if potassium carbonate is employed and the water of reaction is removed by azeotropic distillation. According to Example 1 of U.S. Pat. No. 2,927,943, moderately pure 4-nitrodiphenylamine has been obtained in a yield of 73% of theory in a reaction time of 21 hours under these conditions.

Although the reaction times can be shortened and the yields increased by the addition of various co-catalysts, the successes achieved in these points are still not yet satisfactory. Furthermore, the energy-intensive azeotropic distillation cannot be dispensed with, this usually also requiring the addition of a hydrocarbon as an entraining agent.

It has now been found that, with a far shorter reaction time, the azeotropic distillation can be dispensed with if a metal from the series comprising Al, Mg and Zn or any desired mixtures or alloys of these metals with one another and/or with Ca or Sn is added to the reaction mixture, preferably in finely disperse form, it also being possible for the alloys to contain small amounts of alkali metal.

The invention relates to a process for the preparation of 4-nitrodiphenylamines of the formula (I)

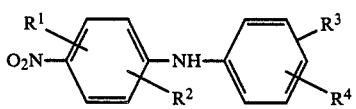

in which
$R^1$, $R^2$, $R^3$ and $R^4$ are identical or different and represent hydrogen or an alkyl radical with 1 to 9 carbon atoms, by reaction of halogenonitrobenzenes of the formula (II)

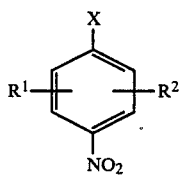

in which
X represents chlorine or bromine, and in which $R^1$ and $R^2$ have the abovementioned meaning, with primary aromatic amines of the formula

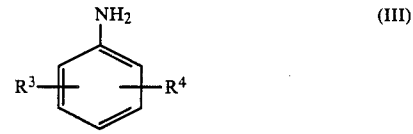

in which
$R^3$ and $R^4$ have the abovementioned meaning, in the presence of potassium carbonate and copper compounds or with the formyl derivatives of the aromatic amines of the formula (III) in the presence of potassium carbonate, characterized in that a metal from the series comprising aluminium, magnesium and zinc or a mixture of two or more of these metals or an alloy of two or more of these metals or an alloy of one or more of these metals with one or more alkali metals and/or with calcium and tin is added, and, preferably, the reaction mixture is worked up without azeotropic distillation.

Preferred metals are aluminium, magnesium and zinc. Alkyl radicals $R_1$ to $R_4$ preferably have 1 to 3C atoms. $R_1$ to $R_4$ denote, in particular, hydrogen.

Examples of possible halogenonitrobenzenes are 4-nitrochlorobenzene, 4-nitrobromobenzene, 4-nitro-2-methylchlorobenzene and 4-nitro-3-methylchlorobenzene.

Examples of possible primary aromatic amines are aniline, o-toluidine, m-toluidine, p-toluidine, 4-ethylaniline, 4-butylaniline, 4-isopropylaniline, 3,5-dimethylaniline and 2,4-dimethylaniline.

The aromatic amines or their formyl derivatives can of course also be employed in the form of mixtures, in particular isomer mixtures. In general about 1 to 6 mol, preferably 1.5 to 4.5 mol and especially 1.7 to 2.5 mol, of the aromatic amine are employed per mol of halogenonitrobenzene.

The process is preferably employed for the preparation of 4-nitrodiphenylamine from 4-nitrochlorobenzene and formanilide.

The metals or metal alloys are employed, in particular, in the form of granules. Their alkali metal content should as far as possible not exceed 5% by weight.

The metals are employed, in particular, in an amount of 105 to 300% of theory, calculated on the amount of the water liberated during the condensation, the calculation being based on the fact that one equivalent of metal bonds one mol of water.

If a formanilide is used as the reaction partner, this is preferably employed in the stoichiometric amount up to a 50% molar excess.

Examples which may be mentioned of the copper catalysts which can be used in the process according to the invention are copper(I) iodide, copper(I) chloride, copper(II) chloride, copper(I) bromide, copper(II) bromide, copper(I) cyanide, copper(I) oxide, copper(II) oxide, copper(II) carbonate, basic copper(II) carbonate, copper(II) sulphate, copper(II) nitrate, copper(II) formate, copper(II) acetate and organic and inorganic coordination compounds of mono- or divalent copper. Oxygen-containing copper compounds, such as copper(II) oxide, copper(II) carbonate, basic copper(II) carbonate or copper(I) oxide are preferably employed, the copper catalyst in general being employed in an amount of 0.001 to 0.1, preferably 0.01 to 0.05, mol per mol of halogenonitrobenzene employed. The copper catalysts can be employed either individually or as a mixture with one another.

Rubidium compounds and caesium compounds can also be added to the reaction mixture in an amount of 0.00003 to 0.006, preferably 0.0001 to 0.001, mol/mol of nitrochlorobenzene. An increase in yield can also be achieved with the addition of these compounds.

Potassium carbonate can be employed in an equivalent amount or in an excess of up to 1.5 times the equivalent amount.

The reaction temperatures of the process according to the invention can vary within wide limits. They are in general 140° to 225° C., preferably 180° to 210° C.

The process according to the invention can be carried out continuously or discontinuously, by customary methods.

The reaction mixture can be worked up by a procedure in which the salts and metal hydroxides in the reaction mixture are separated off at elevated temperature in a physical manner by centrifugation or filtration.

Unreacted halogenonitrobenzene, primary aromatic amine and solvent can be separated off completely from the filtrate in a rotary evaporator or in a spiral tube evaporator under a vacuum of 5 to 50 mbar at a temperature of 150° to 220° C., the nitrodiphenylamines being obtained as a melt and in turn solidifying after cooling. Another possibility is to partly distil the filtrate in vacuo and to separate off the nitrodiphenylamines largely by crystallization. The nitrodiphenylamines are thereby obtained in a highly pure form and can be thus further processed directly.

4-Nitrodiphenylamines can be prepared in high yields and high purity with short reaction times by the process according to the invention. The formation of by-products takes place only to a small degree in the process according to the invention.

The 4-nitrodiphenylamines prepared by the process according to the invention can easily be reduced to aminodiphenylamines by known processes and as such are useful intermediate products for the preparation of, for example, dyestuffs or stabilizers for rubber (compare U.S. Pat. No. 3,163,616).

EXAMPLE 1

0.83 mol of formanilide, 0.50 mol of p-nitrochlorobenzene, 0.34 mol of potassium carbonate and 0.20 mol of aluminium granules were introduced into a reaction vessel and heated to 195° C. and the mixture was stirred at this temperature for 135 minutes. Volatile constituents were distilled off with steam and the residue was washed with a little sodium hydroxide solution and water. 0.45 mol (90% of theory) of 4-nitrodiphenylamine and 0.02 mol of 4,4'-dinitrotriphenylamine were obtained.

EXAMPLE 2

Example 1 was carried out with 0.80 mol of formanilide and, in addition, 0.0003 mol of caesium carbonate. 0.4725 mol of 4-nitrodiphenylamine (94.5% of theory) and 0.018 mol of 4,4'-dinitrotriphenylamine were obtained.

EXAMPLE 3

Example 2 was repeated with 5 g of an alloy of 57% by weight of Al, 20% by weight of Mg, 10% by weight of Ca, 10% by weight of Zn and 3% by weight of K instead of aluminium granules. 94.5% of theory of 4-nitrodiphenylamine was again obtained.

I claim:

1. In the process for the preparation of 4-nitrodiphenylamines of the formula

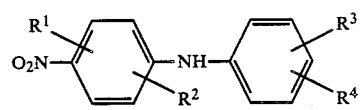

in which
R$^1$, R$^2$, R$^3$ and R$^4$ are identical or different and each represents hydrogen or an alkyl with 1 to 9 carbon atoms, by reaction of halogenonitrobenzenes of the formula

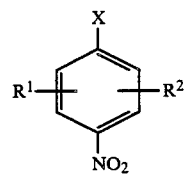

in which
X represents chlorine or bromine, and in which
R$^1$ and R$^2$ have the above-mentioned meaning, with primary aromatic amines of the formula

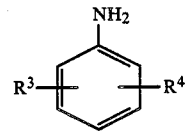

in which
R$^3$ and R$^4$ have the above-mentioned meaning, in the presence of potassium carbonate and copper compounds or with the formyl derivatives of the aromatic amines in the presence of potassium carbonate,
the improvement comprises carrying out the reaction in the presence of a metal comprising aluminium, magnesium or zinc, or a mixture of two or more of these metals, or an alloy of two or more of these metals, or an alloy of one or more of these metals with one or more alkali metals, with or without calcium and tin, the amount of said metals being from 105 to 300% of theory, calculated on the amount of water liberated during the condensation and based on the fact that one equivalent of metal bonds one mol of by-product water, and working up the reaction mixture without azeotropic distillation.

2. Process according to claim 1, characterized in that R$^1$, R$^2$, R$^3$ and R$^4$ denote hydrogen.

3. Process according to claim 1, characterized in that aluminium, magnesium or zinc is employed as the metal.

4. Process according to claim 1, characterized in that formanilide is employed.

* * * * *